United States Patent [19]
Amaratunga et al.

[11] Patent Number: 6,030,819
[45] Date of Patent: Feb. 29, 2000

[54] GENETICALLY ENGINEERED MICROORGANISMS AND METHOD FOR PRODUCING 4-HYDROXYBENZOIC ACID

[75] Inventors: Mohan Amaratunga, Clifton Park; John Henry Lobos, Ballston Spa; Bruce Fletcher Johnson, Scotia; Eric Douglas Williams, Schenectady, all of N.Y.

[73] Assignee: General Electric Company, Schenectady, N.Y.

[21] Appl. No.: 09/161,364

[22] Filed: Sep. 28, 1998

[51] Int. Cl.$^7$ ................................. C12P 7/00; C12P 7/02; C12P 7/22; C12P 7/40; C12P 7/42

[52] U.S. Cl. .................... 435/132; 435/136; 435/146; 435/155; 435/156; 435/252.8; 435/317.1; 435/320.1; 435/849

[58] Field of Search ..................... 435/132, 136, 435/146, 155, 156, 252.8, 317.1, 320.1, 849, FOR 101, FOR 102

[56] References Cited

U.S. PATENT DOCUMENTS 4,681,852   7/1987   Tribe ....................................... 435/108

OTHER PUBLICATIONS

"Inhibition of *Escherichia Coli* by p–Aminobenzoic Acid and its Reversal by p–Hydroxybenzoic Acid", by Bernard D. Davis, M.D., J. Exp. Medicine, pp. 243–254 (1951).

"Toward a Science of Metabolic Engineering", by James E. Bailey, Science 252, pp. 1668–1675 (1991).

"Microbial Production of Specifically Ring. 13C–Labelled 4–Hydroxybenzoic Acid", by R. Muller et al., Appl. Microbiol. Biotechnol. 43: pp. 985–988 (1995).

"Genetic Engineering of Metabolic Pathways Applied to the Production of Phenylalanine", by K. Backman et al., Annals New York Academy of Sciences 589, pp. 16–24 (1990).

"Formation of 4–Hydroxybenzoate in *Escherichia Coli*: Characterization of the ubiC Gene and its Encoded Enzyme Chorismate Pyruvate–lyase", by M. Siebert et al., Microbiology 140: pp. 897–904 (1994).

"Cloning and Sequencing of *Escherichia Coli* ubiC and Purification of Chorismate Lyase", by Brian P. Nichols et al., Journal of Bacteriology 174 (16): pp. 5309–5316 (1992).

*Primary Examiner*—Nathan M. Nutter
*Attorney, Agent, or Firm*—Noreen C. Johnson; Douglas E. Stoner

[57] ABSTRACT

The present invention pertains to a method for economical biofermentative production of 4-hydroxybenzoic acid (PHB) using genetically engineered *E. coli*. According to the invention, a plasmid is provided which controls the overexpression of chorismate pyruvate lyase, the bacterial enzyme which catalyzes the production of PHB from chorismate. Mutant *E. coli* selected with a unique two-step screening assay to overproduce chorismate have been transformed with this plasmid, providing a biocatalyst that efficiently converts glucose to PHB.

17 Claims, 3 Drawing Sheets

GENETICALLY ENGINEERED MICROORGANISMS AND METHOD FOR PRODUCING 4-HYDROXYBENZOIC ACID

This invention was made with Government support under Government Contract No. 70NANB5H1135, awarded by the National Institute of Science and Technology. The Government has certain rights in this invention.

TECHNICAL FIELD

This invention relates to genetically engineered microorganisms and a method for the production of 4-hydroxybenzoic acid, an important monomer used for the production of liquid crystal polymers. In particular, the invention provides a less costly method of producing this important raw material using genetically engineered *Escherichia coli* (*E. coli*) which overproduce it.

BACKGROUND ART

Liquid crystalline polymers (LCPs) are a class of thermoplastics that exhibit a unique combination of properties including good flow, high temperature performance, low mold shrinkage, and excellent chemical resistance which allow them to be useful in many markets. 4-hydroxybenzoic acid (para-hydroxybenzoic acid, PHB) is a key monomer used in the production of LCPs. The cost of this monomer (approximately $2.40/lb) is a major portion of the high cost of LPCS, and limits the commercial applications for which they can be used. A large proportion of the cost of PHB, and consequently LCPs, is related to the cost of its chemical synthesis.

PHB production by chemical synthesis requires petrochemical starting materials, whose cost and availability depend on oil. Because of the uncertainty involved in using a process dependent on fossil fuels, making the considerable investment to increase capacity to achieve economies of scale in PHB production is risky without having predetermined markets for the product and therefore is generally not done. Additional cost in the manufacture of PHB by chemical synthesis is due to the hazardous waste stream which is generated. A new, low cost process to manufacture PHB which does not require petrochemical starting materials and does not generate a hazardous waste stream would overcome these problems and greatly reduce the manufacturing costs of LCPs, allowing them to be used more widely. The inventors have been able to develop such a process for the production of PHB using *E. coli* fermentation.

PHB is produced as a minor metabolite by *E. coli*, however *E. coli* is not capable of excreting PHB at levels high enough to be easily detectable or cost-effectively recovered by conventional commercial methods (less than 2 mg of PHB per liter of medium). Therefore, for biological production of PHB by *E. coli* to be economically feasible, the amount *E. coli* naturally produces must be dramatically increased.

Typically, increased production of a metabolite is achieved by mutating the microorganisms and selecting improved strains from among them using a screening assay. Naturally occurring (spontaneous) mutations also may be taken advantage of when suitable screening methods are available. Both of these methods require the use of effective screening methods to detect clones having the desired characteristics, a very time-consuming and labor-intensive process both in terms of the development of the screening assays and their execution. In fact, the development and manufacturing costs at this stage can sometimes overreach the potential benefits gained from the improvements in the detected mutant strains.

Another approach to increasing production of a desired metabolite is the manipulation of the particular genes involved in the relevant biological pathway. With the evolution of genetic engineering methods, manipulation and overexpression of selected enzymes have become routine. It is now possible to create a biocatalyst in which all the genes necessary to synthesize a particular product are selected and amplified. However, overexpression of a large group of enzymes adds an extra metabolic burden to the microorganism, sometimes resulting in lower overall production due to poor growth and general metabolism of the cells. In addition, selecting and amplifying each enzyme in the synthesis of a product with multiple steps is costly in both time and labor. Thus, it is important to critically select which genes are to be amplified, how they are overexpressed, and how much they are overexpressed.

PHB is biosynthesized from glucose in *E. coli*, as shown in FIG. 1. A significant number of steps are required in the metabolic pathway from 3-deoxy-D-arabino-heptulosonate-7-phosphate to chorismic acid. The final and possibly the rate-limiting step in the synthesis, conversion of chorismate to PHB, is catalyzed by chorismate pyruvate lyase (CPL), the expression product of the ubiC gene.

Cloning and characterization of the ubiC gene product and the entire DNA sequence of the ubiC gene has been reported by Siebert et al., Microbiology 140: 897–904 (1994) and by Nichols and Green, Journal of Bacteriology 174 (16): 5309–5316 (1992). Microbial production of PHB using *Klebsielia pneumoniae* with a plasmid allowing overexpression of CPL also has been reported by Muller et al., Appl. Microbiol. Biotechnol. 43: 985–988 (1995), however, the amount of PHB obtained by this method was only 300 mg/L, insufficient for reasonable commercial production.

In summary, the current methods available to produce PHB either through chemical synthesis, or by biofermentation with *K. pneumoniae*, suffer from serious disadvantages which make the commercial production of PHB too expensive to allow the general use of LCPs. Therefore, there remains a need for a biofermentation process for the synthesis for 4-hydroxybenzoic acid which can produce large amounts of PHB at a commercially reasonable cost.

SUMMARY OF THE INVENTION

Accordingly, one aspect of the present invention is a method of producing 4-hydroxybenzoic acid comprising providing *E. coli* cells; exposing the *E. coli* cells to an aromatic amino acid antimetabolite; performing a first isolation to isolate the *E. coli* cells which survive the exposure to the antimetabolite; exposing the *E. coli* cells isolated in the first isolation to para-aminobenzoic acid; performing a second isolation to isolate the *E. coli* cells which survive the exposure to para-aminobenzoic acid; providing a plasmid which is capable of expressing the ubiC gene product; transforming the *E. coli* cells isolated in the second isolation with the plasmid; and allowing the transformants to ferment in the presence of glucose. Another aspect of the invention is a method of selecting *E. coli* mutants which overproduce 4-hydroxybenzoic acid, comprising providing *E. coli* cells; exposing the *E. coli* cells to an aromatic amino acid antimetabolite; performing a first isolation to isolate the *E. coli* cells which survive the exposure to the antimetabolite; exposing the *E. coli* cells isolated in the first isolation to para-aminobenzoic acid; and performing a secondary isolation to isolate the *E. coli* cells which survive the exposure to the para-aminobenzoic acid. A yet further aspect of this invention provides the plasmid pMCP2 and *E. coli* cells harboring the plasmid pMCP2.

DESCRIPTION OF THE INVENTION

The inventors have developed a biocatalytic method which produces large amounts of PHB during fermentation. The biocatalytic organism both has an increased metabolic carbon flow from glucose towards PHB and overexpresses CPL, an important enzyme in the biosynthesis of PHB. As far as we are aware, this is the first time that modifications in the carbon flow and overexpression of the ubiC gene product have been combined to overproduce PHB in *E. coli*. The inventive biofermentation process using genetically engineered *E. coli* is capable of producing PHB in amounts nearly 40 times greater than that achievable by any prior art method.

Figure 1:
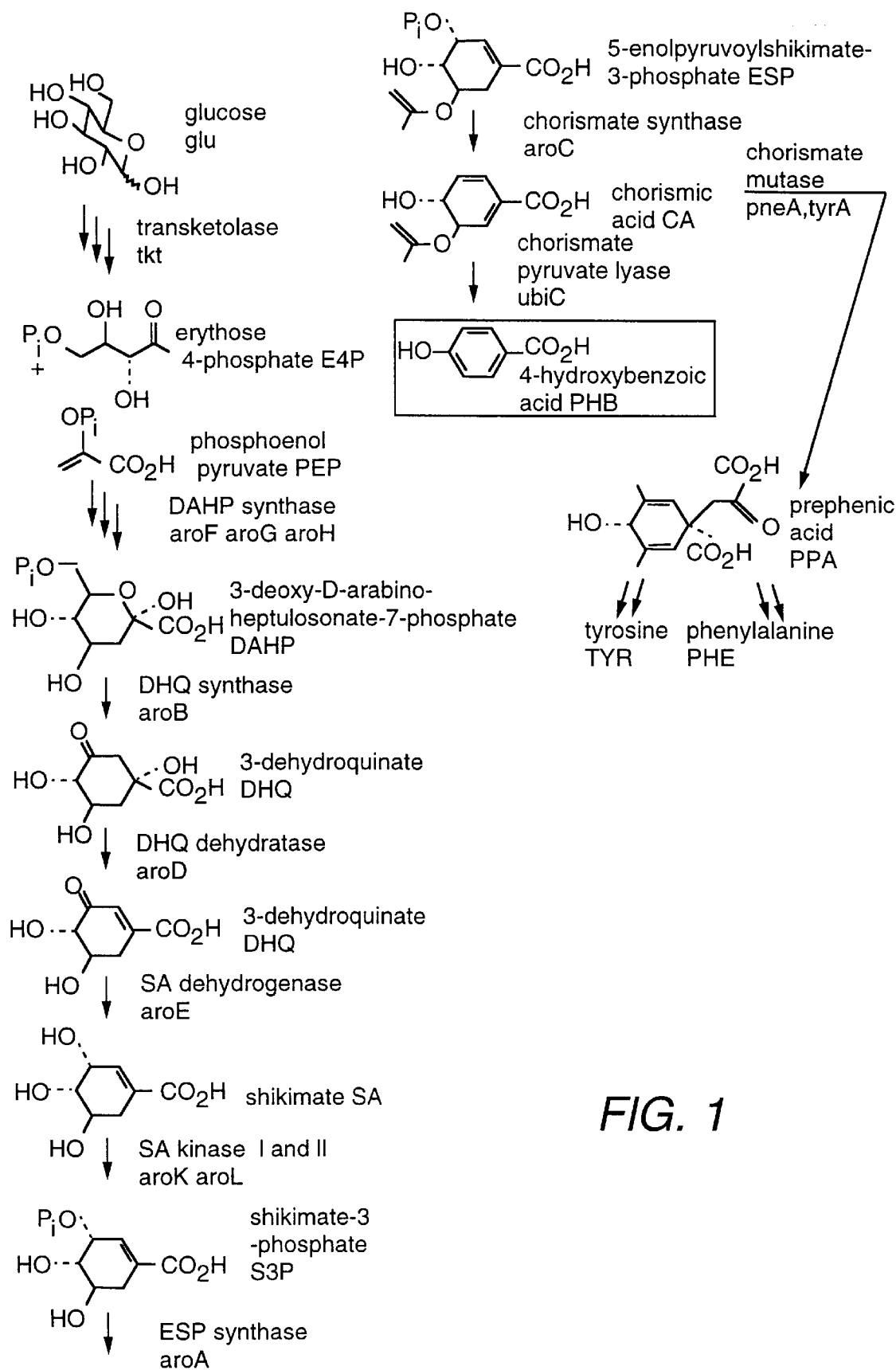
FIG. 1 is a schematic diagram showing the biosynthetic pathway for the production of chorismate, PHB and aromatic amino acids from glucose in *E. coli*.

In *E. coli*, transformation of glucose to PHB involves approximately fifteen different enzymatic steps. FIG. 1 provides a summary of the important intermediates in the pathway. The ubiC gene product, CPL, is a likely candidate for amplification because of the low product turnover of CPL, and because it exists at a major branch in the metabolic pathway. At this point in the biosynthetic pathway, CPL's substrate, chorismate, may be converted to PHB, to prephenic acid (PPA) and the aromatic amino acids, or to a variety of other products. Therefore, increasing the carbon flow of metabolism toward chorismate increases the substrate available for conversion into PHB, and also increases the substrate available to the aromatic amino acid pathway through PPA, and to other products. Thus, cells which produce more chorismate and thus more PHB also produce more aromatic amino acids.

The inventors have taken advantage of this characteristic of PHB metabolism to identify cells which overproduce PHB by first screening for chorismate overproducers using a screening assay which detects an aromatic amino acid. Conveniently, screening methods for phenylalanine overproducers are well documented (U.S. Pat. No. 4,681,852 to David E. Tribe), making it possible to isolate mutants which overproduce phenylalanine easily. This relatively well-characterized and inexpensive assay thus can serve as a simple primary screen for *E. coli* mutants which have increased chorismate production.

The primary screens for organisms which overproduce phenylalanine are based on the phenylalanine antimetabolites, fluorophenylalanine and β2- thienylalanine. Both of these phenylalanine analogs are incorporated into protein in place of phenylalanine and are toxic to *E. coli* unless sufficient excess phenylalanine is present to overwhelm the concentrations of analog. Thus, only those cells which overproduce phenylalanine can survive and grow when cultured in the presence of the antimetabolites. Incubation of about $10^6$ to about $10^9$ cells per 150 mm plate in the presence of about 2 mM to about 10 mM β2-thienylalanine or about 0.5 mM to about 1.2 mM fluorophenylalanine for a period of at least 8 hours up to about seven days results in a surviving cell population selected for phenylalanine over-production. Preferred conditions for this screening assay are $10^7$–$10^8$ cells per 150 mm diameter plate in either 0.6 mM fluorophenylalanine or 5 mM β2-thienylalanine, and incubation for about three days.

It is also possible that cells which overproduce an aromatic amino acid such as phenylalanine do so not because chorismate is being overproduced, but because, for example, PPA or some other aromatic amino acid intermediate subsequent to PPA is being overproduced. Thus, the phenylalanine screening assay alone may produce false positives (cells which overproduce phenylalanine but do not overproduce PHB). A direct secondary screen for chorismate overproduction is therefore necessary to eliminate those cells which do not truly overproduce chorismate and therefore PHB.

The secondary screen for true PHB overproducers among the phenylalanine producers which survived the first screen is based on the PHB antimetabolite, para-aminobenzoic acid (PABA). Similarly to the assay described above, only cells with the ability to synthesize excess PHB will grow in the presence of PABA, which is normally toxic to *E. coli* in high concentrations. In Bernard Davis, J. Exp. Medicine 243–254 (1951), the authors showed that the inhibition of *E. coli* cell growth by PABA was competitively reversed by exogenous PHB. This invention takes advantage of this quality to select PHB overproducers which secrete (endogenous) PHB in the presence of PABA. For this screen to work effectively, the cell density should be less than $10^5$ cells per plate. Therefore, to avoid using thousands of plates to screen $10^9$ or more cells, and to reduce the total cost of screening, the two screen procedure was developed, using a pre-screen for an aromatic amino acid.

The combination of these two screens allowed verified selection and isolation of *E. coli* mutants with an increased metabolic carbon flow from glucose to chorismate. To get maximum PHB production, however, *E. coli* must be able to convert all of the available (overproduced) chorismate into PHB. Natural levels of CPL in *E. coli* are not sufficient to accomplish this. Therefore, the *E. coli* strains which overproduced chorismate were transformed with a plasmid engineered to express the ubiC gene, thereby increasing the CPL activity in the cells.

Figure 2:
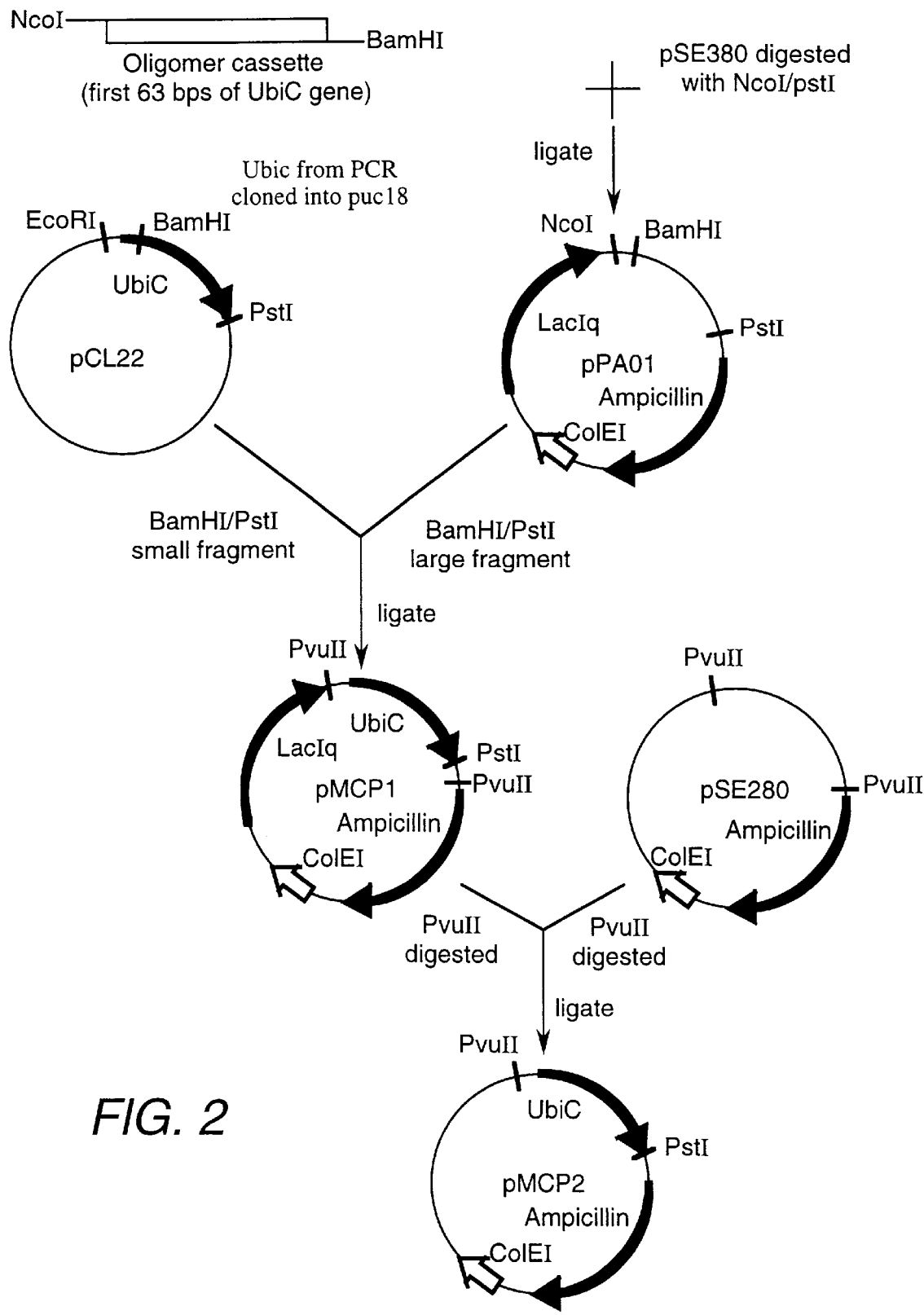
FIG. 2 depicts the construction and subcloning of the CPL (ubiC gene) overproducing plasmid, pMCP2.

This was accomplished by cloning the ubiC gene under a stronger trc promoter as diagramed in FIG. 2. A segment of the ubiC gene had been isolated previously from wild type *E. coli* using standard molecular biology techniques, including PCR, and the published sequence of the gene. For use with this invention, a PCR gene fragment of the ubiC gene was cloned into pUC18 vector, reengineered, and recloned to form a plasmid which can express maximum levels of the ubiC gene product. See Example 2 for details.

The following nonlimiting examples demonstrate the use of the invention. Other related methods within the scope of the invention will be apparent to those of skill in the art.

EXAMPLES

1. Screening of *E. coli* Cells and Isolation of Clones Overproducing PHB

To isolate mutants with increased phenylalanine synthesis, a large number of wild type *E. coli* cells were plated on agar/glucose plates with either 0.6 mM fluorophenylalanine or 5 mM β2-thienylalanine, concentrations which are toxic to cells producing ordinary amounts of phenylalanine. E. coli cells were plated to a final cell density of between $10^7$ and $10^8$ cells per 150 mm plate. Plates then were incubated for 3 days at 37° C. Typically, 1 to 10 colonies per plate survived after the three-day period.

The surviving colonies were then assayed for overproduction of PHB by plating on succinate with 10 mM para-aminobenzoic acid (PABA). The positive colonies from the first assay were pooled in groups of about ten in each PABA/succinate plate to reduce the amount of PABA required for the assays. For plating, the pools of cells were grown in 5 mL Luria Broth. Cell pellets were washed twice with 2 mL M9 salt solution (6 g/L $Na_2HPO_4$, 3 g/L $KH_2PO_4$, 0.5 g/L NaCl, 1 g/L $NH_4Cl$) and plated on agar/0.4% succinate plates containing 10 mM PABA and 10 ug/mL aspartate at a density of $10^3$ cells per 150 mm plate. Colonies visible on the plates after incubation for 4 days at 37° C. were removed. These colonies were grown overnight to a final density of approximately $10^8$ cells/mL in 5 mL M9 salt solution containing 0.4% glucose with shaking at 37° C. The supernatants then were assayed for PHB using a colorimetric assay as follows. Unknown PHB solution or known standard PHB solutions (800 $\mu$L) in Tris, pH 7.1, were mixed with 100 $\mu$L 20 mM 4-antiaminopyrine. The solutions were incubated at room temperature for about one minute, and then mixed with 100 $\mu$L 300 mM $NaIO_4$. Absorbance at 492 nm was measured and the PHB concentrate calculated. PHB unknowns were diluted if necessary to yield a solution between about 0.1 mM to about 0.8 mM, the approximate range for which this assay is linear. Selected supernatants were also analyzed by HPLC for aromatic amino acids and PHB.

Wild type E. coli did not excrete detectable levels of amino acids or PHB to the medium, as shown in Table 1. Most of the selected mutants which were tested, however, did overproduce PHB. Two representative cell lines, JP01 and JP02, selected by our screens for overproduction of PHB, produced greatly increased levels of both aromatic amino acids and PHB as detected by HPLC. See Table 1. These results indicate that in these cells, at least some of the metabolic controls on the carbon flow from glucose to the chorismate pathway have been released.

TABLE 1

Secretion of PHB, Phenylalanine, and Tyrosine by Wild
Type E. coli and Selected PHB Overproducers into Culture Media.

| Cell Line | PHB ($\mu$M) | Phenylalanine ($\mu$M) | Tyrosine ($\mu$M) |
|---|---|---|---|
| Wild Type | nd* | nd* | nd* |
| JP01 | 7.7 | 129 | nd* |
| JP02 | 14.5 | 128 | 82 |

*nd = not detectable, less than 3 mg/L.

2. Construction and Subcloning of a CPL (ubiC gene) Overproducing Plasmid

A PCR DNA fragment containing the ubiC gene was cloned into pUC18 vector, creating pCL22 plasmid. See FIG. 2. Due to misalignment of the gene and the promotor, the level of expression of the gene product from this plasmid was not optimal. Therefore, the ubiC gene was subcloned into plasmid pSE380 (Invitrogen) as shown in FIG. 2, forming plasmid pMA01. Initially, a chemically synthesized gene segment containing the first 63 base pairs of the ubiC gene with NcoI and PstI sticky ends was prepared. This was cloned into pSE380 plasmid (Invitrogen) digested with NcoI and PstI (Ncol/pstl), and this recombinant plasmid then was transformed into E. coli competent cells. The supercoiled plasmid from this construct was isolated using well known standard molecular biology techniques and digested with BamHl and PstI. The resulting large linear fragment was ligated with the small fragment from a BamHl and PstI digest of the ubiC-pCU construct. This resulting plasmid, pMCP1, expresses CPL protein under the trc promoter, however in this construct, isopropylthiogalactoside (IPTG) induction is necessary to obtain the maximum level of expression. To eliminate this IPTG control, the PvuII fragment from pMCP1 was recloned to PvuII digested pSE280 (Invitrogen). This final plasmid, pMCP2, was able to express maximum levels of CPL without IPTG induction.

3. Overexpression of ubiC Gene in E.coli

E.coli mutant colonies which had previously been selected for overproduction of PHB as described in Example 1 were transformed with the plasmid of Example 2 using traditional molecular biology methods. As a result of transforming the pMCP2 plasmid to two mutated strains, the JP01/pMCP2 series and the JP02/pMCP2 series were created. These transformants were tested for their ability to make PHB in shake flask cultures as follows. All constructs were tested in 250 ml shake flasks at 37° C. in 50 ml SMM (10.0 g/L glucose, 1.0 g/L yeast extract, 12.0 g/L $K_2HPO_4$, 3.0 g/L $KH_2PO_4$, 1.0 g/L $MgCl_2.6H2O$, 4.0 g/L $(NH_4)_2SO_4$, 0.5 g/L $CaCl_2.2H_2O$, 0.4 mg/L $CuSO_4.5H_2O$, 0.5 mg/L $ZnSO_4.7H_2O$, 25.0 mg/L $MnSO_4.H_2O$, 1.0 mg/L $CoCl_2.6H_2O$, 0.2 mg/L sodium molybdate.$2H_2O$, 50.0 mg/L $FeSO_4.7H_2O$, 50.0 mg/L sodium citrate.$2H_2O$, 100 mg/L carbenicillin, and 1.0 ml/L Hodag M10 antifoam) containing 1% glucose, with agitation of 300 rpm. After incubation for 24 hours, culture supernatants were sedimented to remove particulates and assayed for PHB, phenylalanine and tyrosine using HPLC.

TABLE 2

Production of PHB, Phenylalanine, and Tyrosine by
Mutant E. coli Transformed with Plasmid pMCP2.

| Cell Line | PHB ($\mu$M) | Phenylalanine ($\mu$M) | Tyrosine ($\mu$M) |
|---|---|---|---|
| Wild Type-1/pMCP2 | 119 | nd* | 70 |
| JP01A/pMCP2 | 486 | nd* | 15 |
| JP01B/pMCP2 | 915 | 169 | 104 |
| JP01C/pMCP2 | 310 | 73 | nd* |
| JP02A/pMCP2 | 403 | nd* | nd* |
| JP02B/pMCP2 | 666 | 96 | 45 |

*nd = not detectible, less than 3 mg/L.

Results showed that biocatalysts according to the invention can produce markedly increased amounts of PHB. See Table 2. Transformation of wild type E. coli improved the production of PHB (compare the first lines of Tables 1 and 2). However, mutations to the chorismate pathway combined with transformation of the mutated cells with the plasmid overexpressing CPL resulted in dramatically improved PHB production. The highest levels of PHB were obtained in one strain combining the mutant E. coli cell line JP01 with the pMCP2 plasmid (see the data for JP01LB/pMCP2). This strain was tested for the ability to produce high concentrations of PHB in a pilot scale fermentation.

4. Biocatalytic Production of PHB by a Transformed E. coli Cell Line

JP01B/pMCP2 cells for the fermentation were revived from a frozen stock culture stored at −80° C. in 30% glycerol. The cultures were first grown up in 5 ml tubes of Luria broth containing 100 mg/L carbenicillin for 8 h. A 1% (v/v) inoculum of these cells (approximately $10^8$ cells/mL) was added to 1 liter baffled shaker flasks containing 300 mL fermentation medium (SMM) as described above, but lacking Hodag M10 antifoam. The baffled shaker flasks were incubated at 37° C. with vigorous shaking (300 rpm) for 10 hours before addition to the fermentors as described in Example 3.

The antibiotic carbenicillin was added to the SMM initially to maintain cells containing the ampicillin resistance gene which is present on the pMCP2 plasmid. The fermentor held an initial volume of 3.5 L of this medium before inoculation. The initial conditions for the fermentor were 37° C., pH 7.0, agitation at 500 rpm, and air sparged at a rate of 5.0 L/h. Glucose concentration was 1.0% (w/v). A pH of 7.0 was maintained and controlled with the addition of 30% ammonium hydroxide throughout the During thn.

During the first 6 hours of fermentation, the dissolved oxygen (DO) was maintained at 20% of saturation (~2 ppm $O_2$) by sparging with air. At approximately 6 hours, after the initial glucose to was consumed, a 60% glucose solution (w/v) was pumped into the fermentor, according to the DO-Stat method. This method controls the rate of glucose addition so that glucose is limited throughout the fermentation: as the DO increased above the set point (20% in this case), the glucose feed was increased until the DO returned to the set is point. When the DO dropped below the set point, the glucose feed rate was reduced. Also, beginning at 6 hours of fermentation the agitation was gradually increased to 900 rpm over a period of 4 hours. Beginning at 10 hours of fermentation, the temperature of the fermentor was gradually reduced to 35° C. over 2 hours. The fermentation continued under these conditions for over 50 hours. During the 50 hour fermentation, 1.6 L of 60% glucose solution (1020 g of glucose) was consumed by the cells.

Figure 3:
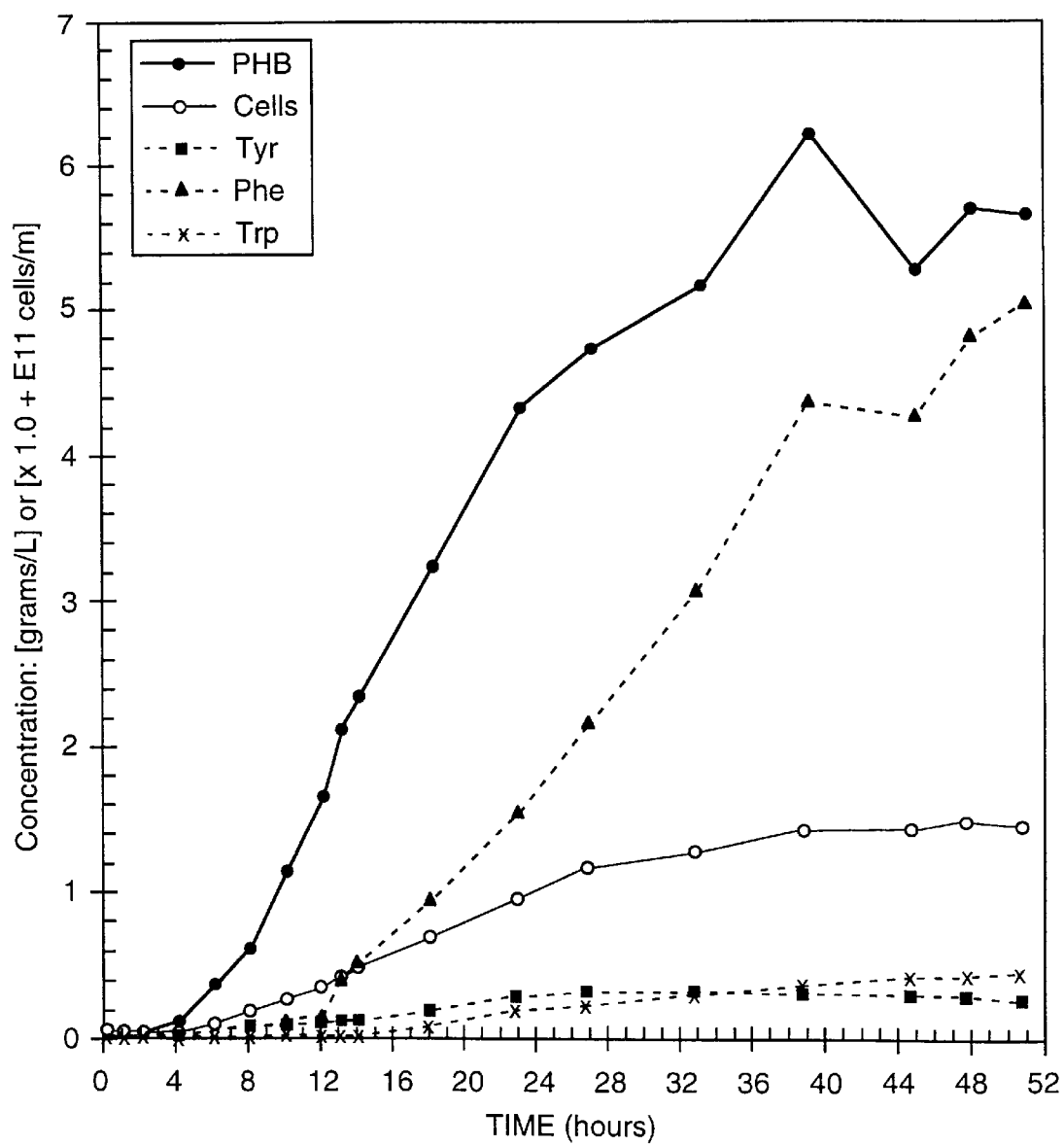
FIG. 3 provides the concentrations of PHB, phenylalanine, tryptophan and tyrosine produced during a 50 hour fermentation of *E. coli*, strain JP01B/pMCP2. Number of cells present is also indicated.

Cell concentration and the formation of PHB and the aromatic amino acids phenylalanine, tyrosine and tryptophan were monitored continuously during the course of the fermentation. These data are provided in FIG. 3. PHB production steadily continued over the first 40 hours of the fermentation and reached a plateau at a concentration of 6.2 g/L after that time. Decreases in the PHB concentration occurred during the last 10 hours due to dilution of the fermentation medium by the continued addition of glucose solution without further relative production of PHB. After 50 hours, approximately 3.0% of the glucose was converted to PHB, however, during the first 40 hours of fermentation, the yield of PHB with respect to glucose was almost 4.0%.

We claim:

1. A method of producing 4-hydroxybenzoic acid, comprising:
   a) providing *E. coli* cells;
   b) exposing the *E. coli* cells to an aromatic amino acid antimetabolite;
   c) performing a first isolation to isolate the *E. coli* cells which survive the exposure to the antimetabolite;
   d) exposing the *E. coli* cells isolated in the first isolation to para-aminobenzoic acid;
   e) performing a second isolation to isolate the *E. coli* cells which survive the exposure to para-aminobenzoic acid;
   f) providing a plasmid which is capable of expressing the ubiC gene product;
   g) transforming the *E. coli* cells isolated in the second isolation with the plasmid; and
   h) allowing the transformants to ferment in the presence of glucose.

2. A method according to claim 1, wherein the aromatic amino acid antimetabolite is selected from the group consisting of fluorophenylalanine and β2-thienylalanine.

3. A method according to claim 2, wherein the aromatic amino acid antimetabolite is about 0.5 mM to about 1.2 mM fluorophenylalanine.

4. A method according to claim 3, wherein the aromatic amino acid metabolite is about 0.6 mM fluoropenylalanine.

5. A method according to claim 2, wherein the aromatic amino acid antimetabolite is about 2 mM to about 10 mM β2-thienylalanine.

6. A method according to claim 5, wherein the aromatic amino acid metabolite is 5 mM β2-thienylalanine.

7. A method according to claim 1, wherein the exposure to an aromatic amino acid antimetabolite is for a period of about 8 hours to about 7 days.

8. A method according to claim 7, wherein the exposure to an aromatic amino acid antimetabolite is for a period of about 3 days.

9. A method according to claim 1, wherein the plasmid which is capable of expressing the ubiC gene product is pMCP2.

10. The plasmid pMCP2.

11. An *E. coli* cell harboring the plasmid according to claim 10.

12. A method of selecting *E. coli* mutants which overproduce 4-hydroxybenzoic acid, comprising:
    a) providing *E. coli* cells;
    b) exposing the *E. coli* cells to an aromatic amino acid antimetabolite;
    c) performing a first isolation to isolate the *E. coli* cells which survive the exposure to the antimetabolite;
    d) exposing the *E. coli* cells isolated in the first isolation to para-aminobenzoic acid; and
    e) performing a second isolation to isolate the *E. coli* cells which survive the exposure to the para-aminobenzoic acid.

13. A method according to claim 12, wherein the aromatic amino acid antimetabolite is selected from the group consisting of fluorophenylalanine and β2-thienylalanine.

14. A method according to claim 13, wherein the aromatic amino acid antimetabolite is fluorophenylalanine.

15. A method according to claim 13, wherein the aromatic amino acid antimetabolite is β2-thienylalanine.

16. *E. coli* cells selected according to the method of claim 12.

17. *E. coli* cells according to claim 16, wherein the cells contain the plasmid pMCP2.

* * * * *